United States Patent [19]

Matsumoto et al.

[11] Patent Number: 5,391,769

[45] Date of Patent: Feb. 21, 1995

[54] METHOD OF PREPARING 3-DPA-LACTONE

[75] Inventors: Katsuya Matsumoto; Takashi Ebata; Hiroshi Kawakami; Koshi Koseki; Hajime Matsushita, all of Yokohama, Japan

[73] Assignee: Japan Tobacco Incorporated, Tokyo, Japan

[21] Appl. No.: 987,277

[22] PCT Filed: Jul. 21, 1992

[86] PCT No.: PCT/JP92/00925

§ 371 Date: Mar. 10, 1993

§ 102(e) Date: Mar. 10, 1993

[87] PCT Pub. No.: WO93/02070

PCT Pub. Date: Feb. 4, 1993

[30] Foreign Application Priority Data

Jul. 22, 1991 [JP] Japan ................... 3-204601

[51] Int. Cl.$^6$ ........................................... C07D 305/12
[52] U.S. Cl. .................................................. 549/313
[58] Field of Search ........................................ 549/313

[56] References Cited

U.S. PATENT DOCUMENTS 4,859,677  8/1989  Borchardt et al. ................. 549/313

Primary Examiner—C. Warren Ivy
Assistant Examiner—Raymond Covington
Attorney, Agent, or Firm—Birch, Stewart, Kolasch & Birch

[57] ABSTRACT

The present invention discloses a method of preparing 3-DPA-lactone, which is difficult to obtain in a large amount from nature. According to the method of the present invention, the target compound can be synthesized at a high yield in fewer steps and more easily than by the conventional synthesizing technique, and selectively from a widely available material. In the method of the present invention, the hydroxyl groups at the 2- and 5 -positions of γ-ribonolactone are protected, and then the hydroxyl group at the 3-position is eliminated so as to form a double bond between the 2- and 3-positions. After that, the protecting groups for the hydroxyl groups are eliminated.

20 Claims, No Drawings

METHOD OF PREPARING 3-DPA-LACTONE

DESCRIPTION

1. Technical Field

The present invention relates to a method of preparing 3-DPA-lactone.

2. Background Art

Recently, in the field of fine chemicals such as medicines, pesticides and so on, a great deal of attention has been focused on glycoside compounds and sugar-analogue compounds which exist naturally as useful biological active substances.

A well-known example of the sugar-analogue compounds is (2S, 4S)-2-hydroxy-4-hydroxymethyl-4-butanolide which is represented by the following formula [5]. The common name for this compound is 3-deoxy pentonic acid lactone, usually abbreviated as 3-DPA-lactone.

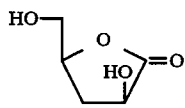

[5]

3-DPA-lactone is known as an endogenous feeding promoter substance present in the body fluid of animals. For example, as set forth in the following documents, the concentration of 3-DPA-lactone in the blood of a rat increased as the duration of fasting of the rat was increased, thereby indicating that 3-DPA-lactone is a feeding promotor. When the substance was administered to a rat, under normal feeding conditions it was observed that feeding behavior of the rat was induced.

(1) Hiroshi OHMURA and Noriaki SHIMIZU; "Chemistry and Biology", Vol. 22, No. 4, page 228

(2) O. Uchikawa, N. Okukado, T. Sakata, K. Arase, K. Terada; "Bull. Chem. Soc. Jpn., 61,2025 (1988)

Therefore, 3-DPA-lactone is an essential substance for making a scientific explanation of feeding behavior of animals including human. The information obtained in the research can be applied widely for development of foods, medicines, and pesticides.

Utilizing its feeding promotion effect, it is possible to promote growth of domestic animals by, for example, mixing the compound into stock feed.

However, 3-DPA-lactone exists in a small amount in nature, and it is difficult to obtain a large amount thereof by extraction from natural material.

Consequently, 3-DPA-lactone must be prepared by a synthetic method. At present, there are two known techniques for preparing 3-DPA-lactone.

One known technique for preparing 3-DPA-lactone L-malic acid having an optical activity as the starting material [O. Uchikawa, N. Okukado, T. Sakata, K. Arase, K. Terada; Bull. Chem. Soc. Jpn., 61,2025 (1988)]. In this method, a vinyl group is introduced to a carbonyl group of (S)-3,4-O-isopropyliden-3,4-dihydroxybutanal by Grignard reaction so as to form the hydroxyl group corresponding to the hydroxyl group at 2-position of 3-DPA-lactone. Then, the vinyl group is oxidatively cleaved using a Sharpless oxidation into a carboxyl group to form γ-lactone.

The other known method for preparing 3DPA-lactone utilizes γ-ribonolactone as the starting material [K. Bock, I. Lundt, C. Pedersen; Acta. Chem. Scand., B 35, 155 (1981)]. In this method, a hydroxy group of γ-ribonolactone is protected by an acetyl group, and then the γ-ribonolactone is subjected to catalytic hydrogenation at high pressure in the presence of palladium carbon which serves as the catalyst. Lastly, after removal of the acetyl group, 3-DPA-lactone is prepared.

However, each of the above-described methods entails the following drawback.

In the synthetic route of the first method proposed by O. Uchikawa et al., the Grignard reaction is not stereoselective, and therefore two types of diasteromers are formed which respect to the hydroxy group at the 2-position. Therefore, it is necessary to separate the two isomers after lactone formation, wherein the yield of the target product having the S configuration of carbon at the 2-position is as low as about 30%. Further, the hydroxyaldehyde having an optical activatity, which is an intermediate, can be obtained through 6 steps from L-malic acid, and the yield thereof is also as low as 25%. In total, it takes 11 steps to prepare 3-DPA-lactone from L-malic acid, and after separation of the diastereomers from each other as set forth above, the overall yield is as low as only 4%.

On the other hand, in the synthetic route of the second method proposed by K. Bock et al., hydrogenation must be carried out at a pressure of as high as 100 atmospheres. Therefore, the; an apparatus used for carrying out the method entails drawbacks in terms of simplicity and safety. In addition, there are many steps involved in this method, and the yield of the product is low.

DISCLOSURE OF THE INVENTION

The object of the present invention is to provide a method of preparing 3-DPA-lactone, wherein the 3-DPA-lactone product can be synthesized easily and selectively from a widely available material at a high yield.

The authors of the present invention conducted extensive studies to achieve the above object, and have discovered a synthetic route for preparing 3-DPA-lactone by fewer steps than the conventional preparation method and at a higher yield, by using γ-ribonolactone as a starting material, and by protecting a hydroxyl group, elimination, catalytic hydrogenation, etc. in a regioselective or stereoselective manner.

The method of preparing 3-DPA-lactone according to the present invention includes the following steps (a)-(d).

(a) protecting the hydroxyl groups located at the 2- and 5-positions of γ-ribonolactone represented by the following formula [1],

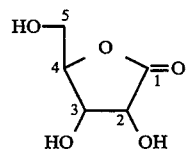

[1]

so as to afford a compound represented by the following formula [2],

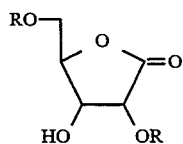

[2]

where R represents a protecting group for a hydroxyl group.

(b) Eliminating the hydroxyl group at the 3-position of the compound represented by the above formula [2] so as to form a double bond between the 2- and 3-positions, and thus giving a compound represented by the following formula [3],

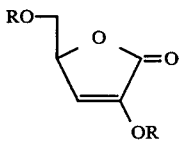  [3]

where R represents a protecting group for a hydroxyl group.

(c) Reducing the double bond between the 2- and 3-position of the compound represented by the above formula [3] so as to give a compound represented by the following formula [4],

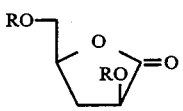  [4]

where R represents a protecting group for a hydroxyl group.

(d) Eliminating the protecting groups of the compound represented by the above formula [4] so as to give a compound represented by the following formula [5],

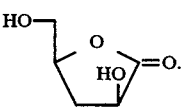  [5]

The above steps of the method of preparing 3-DPA-lactone according to the present invention will now be described in detail.

In step (a), a protecting group R is introduced to the hydroxyl groups at the 2- and 5-positions of γ-ribonolactone represented by the above formula [1].

The protecting group R may be of any type so long as it typically used for the protection of a hydroxyl group. Some preferable examples are acetyl, pivaloyl, benzoyl, 3,5-dinitrobenzoyl, and tert-butyl-diphenylsilyl.

The solvent used for introduction of the protecting group R is not particularly limited, wherein any organic solvents which is generally used can be employed.

The reaction involved in step (a) may be carried out at a temperature of 0°–40° C., for a time period of 10–120 minutes, using 2–3 equivalents of a reagent containing the protecting group R per one equivalent of the γ-ribonolactone.

In step (b), the hydroxyl group located at the 3-position of the compound represented by the above formula [2] and obtained in the step (a) is eliminated (β-elimination), thereby forming a double bond between the 2- and 3-positions.

The β-elimination can be easily performed by converting the hydroxy group at 3-position of the compound of the formula [2] into a leaving group, in the presence of a basic compound.

The leaving group may be arbitrary as far as it is a functional group capable of causing the elimination reaction of the hydroxyl group at 3-position in the presence of a basic compound. Some examples of the leaving group are acyloxy group, as well as those containing a sulfonyl group which are formed by substituting a hydrogen atom of the hydroxyl group with a mesyl group, tosyl group, trifluoromethanesulfonyl group or the like. Preferable leaving groups are those formed by using a mesyl group, tosyl group, and trifluoromethanesulfonyl group.

The reaction involved in step (b) should be carried out using 1–10 equivalents of a compound for introducing the leaving group per one equivalent of the compound represented by the above formula [2], at a temperature of 0°–40° C., preferably, room temperature, and for a time period of 0.5–20 hours.

Although not particularly limited to these, liquid tertiary amine compounds such as pyridine, or widely-used organic solvents containing a basic compound can be used as a solvent in the elimination reaction.

Thus, the compound represented by the above formula [3] can be obtained by the β-elimination, which is caused by the action of the leaving group in the presence of a basic compound.

It should be noted that step (b) may be carried out after step (a) as a separate step, or may be performed simultaneously with step (a).

In the following step (c), the double bond between the 2- and 3-positions of the compound represented by the above formula [3] is reduced to obtain a compound represented by the above formula [4].

One of the reduction method used here in is catalytic hydrogenation, which can be easily performed by adding the compound together with an appropriate metal catalyst, such as platinum, palladium, rhodium, or ruthenium, into an appropriate organic solvent under hydrogen atmosphere, and stirring at about room temperature.

The solvent used here, is not particularly restricted, wherein widely-used organic solvents such as ethyl acetate, ethanol, and methanol can be used.

The reaction in this step should be carried out using 0.01–1 equivalent of the metal catalyst per one equivalent of the compound represented by the above formula [3], at a temperature of 10°–40° C., and for a time period of 0.5–15 hours.

In the final step (d), the protecting group having introduced to the hydroxyl group at each of the 2-and 5-positions of the compound represented by the above formula [4] is eliminated, thereby obtaining 3-DPA-lactone represented by the above formula [5].

The reaction conditions for eliminating the protection group may be those usually set for eliminating an acyl group or silyl group, and are not particularly limited. For example, elimination of an acyl group can be conducted in an aqueous solution under a basic condition, using a metal hydroxide such as sodium hydroxide or potassium hydroxide, a metal carbonate such as sodium carbonate or potassium carbonate, a metal alkoxide such as sodium methoxide or potassium butoxide, or ammonium water, or under an acidic condition using a solution containing hydrochloric acid, paratoluenesulfonic acid, or the like, or in an organic solvent such as alcohol under an acidic condition.

The product thus obtained was examined in terms of optical rotation, $^1$H-NMR spectrum, and $^{13}$C-NMR spectrum, and the measured values were compared with the data in the literature [O. Uchikawa, N.

Okukado, T. Sakata, K. Arase, K. Terada, Bull. Chem. Soc. Jpn., 61,2025 (1988)]. Thus, it was confirmed that the product was 3-DPA-lactone.

Best Mode of Carrying Out the Invention

The present invention will now be described in more detail with reference to an example.

The example discusses a case where the hydroxy group at each of the 2- and 5-positions is protected by a pivaloyl group in step (a), and an elimination reaction is carried out while converting the hydroxyl group at 3-position into a mesyl group in the step (b).

Step (a)

Synthesis of 2,5-O-dipivaloyl-ribonolactone 1.03 g (6.75 mmol) of ribonolactone was dissolved into 16 ml of pyridine, and 2.04 g (16.89 mmol) of pivaloylchloride was further added dropwise under ice-cooling. The solution was then stirred for 30 minutes at room temperature.

Step (b)

3.09 g (26.98 mmol) of mesylchloride was added dropwise to the reaction mixture obtained in step (a) under ice-cooling. The solution was then stirred for 3 hours at room temperature.

The obtained reaction mixture was poured into ice water, and extracted with diethylether. The extract was washed with in hydrochloric acid, sodium bicarbonate aqueous solution, water, saturated copper sulfate aqueous solution, and water in the mentioned order, and dried over magnesium sulfate. The solvent was removed by evaporation under a reduced pressure.

Thereafter, the residue was purified by means of silica gel column chromatography (hexane: ethyl acetate=6:1), followed by recrystallization from a hexane:-diethylether mixture solvent, thereby giving 1.26 g (the yield from starting material was 62.8 %) of the compound represented by the following formula [6].

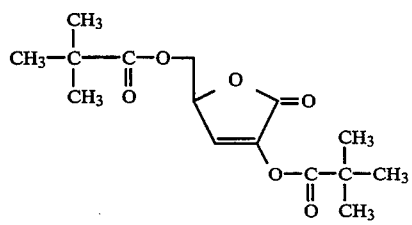

The physico-chemical properties of the compound represented by the above formula [6] are as follows:

Melting Point: 66.0°–67.5° C. $[\alpha]^{26}D$: $-32.6°$ (c=3.07, CHCl$_3$) $^1$H-NMR (CDCl$_3$, ppm from TMS): (CH$_3$)$_3$CO; 1.18 (9H, s), 1.33 (9H, s), 3-position; 7.14 (1H, d, J=2.0 Hz), 4-position; 5.22 (1H, dd, J=2.0, 4.1 Hz), 5-position; 4.37 (2H, d, J=4.1 Hz)

Step (c)

6.39 g (23.23 mmol) of the compound represented by the above formula [6] was dissolved into 70 ml of ethyl acetate, and 0.70 g of 10% palladium-carbon was further added. The mixture was stirred for 2 hours in a hydrogen gas atmosphere at room temperature.

Thereafter, palladium-carbon was filtrated off from the reaction mixture, and the solvent was removed from the filtrate by evaporation under a reduced pressure.

Thereafter, the residue was purified by means of silica gel column chromatography (hexane: ethyl acetate=6:1), followed by recrystallization from a hexane:-diethylether mixture solvent, then 7.16 g of the compound represented by the following formula [7] was obtained.

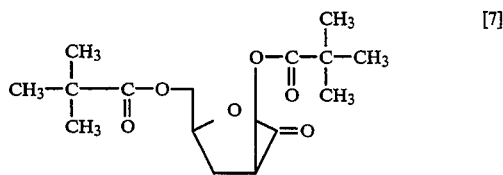

The physico-chemical properties of the compound represented by the above formula [6] were as follows:

Melting Point: 78.0°–80.0° C. $[\alpha]^{25}D$: $+45.9°$ (c=3.07, CHCl$_3$) $^1$H-NMR (CDCl$_3$, ppm from TMS): (CH$_3$)$_3$CO; 1.23 (9H, s), 1.26 (9H, s), 2-position; 5.50 (1H, dd, J=9.0, 10.0 Hz) 3-position; 2.03 (1H, ddd, J=10.0, 10.0, 12.8 Hz), 2.77 (1H, ddd, J=6.1, 9.0, 12.8Hz), 4-position; 4.65–4.73 (1H, m), 5-position; 4.20 (1H, dd, J=5.6, 12.3 Hz), 4.38 (1H, dd, J=3.3, 12.3 Hz)

Step (d)

10.55 g of the compound represented by the above formula [7] was dissolved into 53.7 ml of ethyl acetate, and 53.7 ml of 10% sodium hydroxide aqueous solution was further added. The mixture was stirred for 20 hours at room temperature.

Then, the reaction mixture was acidified by adding 1N hydrochloric acid dropwise thereto under cooling the mixture with ice water.

Thereafter, the solvent was removed from the reaction mixture by evaporation under a reduced pressure, and the residue was purified by means of silica gel column chromatography (ethyl acetate). Thus, 4.53 g (yield of 97.6%) of (2S, 4S)-2-hydroxy-4-hydroxymethyl-4-butanolide (3-DPA-lactone) was obtained.

The physico-chemical properties of the obtained compound were as follows:

$[\alpha]^{28}D$: $+22.6°$ (c=3.07, CH$_3$OH) $^1$H-NMR (CD$_3$OD, ppm from TMS): 2-position; 4.56 (1H, dd, J=8.6, 10.8 Hz) 3-position; 1.92–2.04 (1H, m), 2.54 (1H, ddd, J=5.5, 8.5, 12.5 HZ), 4-position; 4.42–4.50 (1H, m), 5-position; 3.59 (1H, dd, J=5.0, 12.6 Hz), 3.80 (1H, dd, J=2.8, 12.6 Hz) $^{13}$C-NMR [(CD$_3$OD, ppm from CD$_3$OD (CD$_3$; 49.8ppm)]: 179.9, 79.4, 70.1, 64.6, 34.4

As described above, according to the present invention, there is provided a method of preparing 3-DPA-lactone, which is difficult to be obtained in a large amount from nature, the target compound can be synthesized easily and selectively at high yield from a widely available material.

As set forth in the beginning, in the field of fine chemicals such as medicines, pesticides an so on, a great deal of attention has recently been focused on glycoside compounds and sugar-analogue compounds as useful biologically active substances. Under such circumstances, the present invention can easily provide 3-DPA-lactone, which is one of the useful bioactive substances and is known as a feeding promoter substance.

We claim:

1. A method of preparing 3-DPA-lactone comprising the following steps (a)–(d):
   (a) protecting the hydroxyl groups located at the 2- and 5-positions of γ-ribonolactone represented by formula (1),

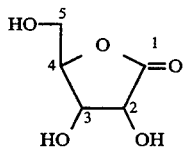
(1)

to yield a compound represented by the following formula (2),

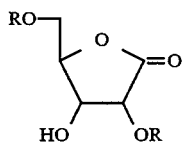
(2)

wherein R represents a protecting group for a hydroxyl group, (b) eliminating the hydroxyl group at the 3-position of the compound represented by formula (2) so as to form a double bond between the 2- and 3-positions, and thus yielding a compound represented by formula (3),

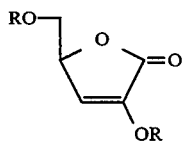
(3)

wherein R represents a protecting group for a hydroxyl group, (c) reducing the double bond between the 2- and 3-positions of the compound represented by formula (3) to yield a compound represented by formula (4),

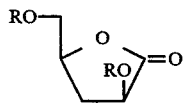
(4)

wherein R represents a protecting group for a hydroxyl group, and (d) eliminating the protecting groups of the compound represented by formula (4) to yield a compound represented by formula (5),

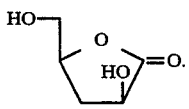
(5)

2. The method of preparing 3-DPA-lactone according to claim 1, wherein said protecting group R is selected from the group consisting of acetyl, pivaloyl, benzoyl, 3,5-dinitrobenzoyl, and tert-butyl-diphenylsilyl.

3. The method of preparing 3-DPA-lactone according to claim 1, wherein in step (b), the elimination of the hydroxyl group at the 3-position of the compound represented by formula (2), is carried out in the presence of a basic compound by β-elimination after converting the hydroxyl group at the 3-position of the compound represented by the formula (2) into a leaving group.

4. The method of preparing 3-DPA-lactone according to claim 3, wherein said leaving group is formed by substituting a hydrogen atom of the hydroxyl group with a group selected from the group consisting of mesyl group, tosyl group, trifluoromethane-sulfonyl group and acyl group.

5. The method of preparing 3-DPA-lactone according to claim 1, wherein step (b) is carried out after step (a) as a separate step.

6. The method of preparing 3-DPA-lactone according to claim 1, wherein step (b) is carried out simultaneously with step (a).

7. The method of preparing 3-DPA-lactone according to claim 1, wherein the reduction of the double bond between the 2- and 3-positions of the compound represented by formula (3) is performed by catalytic hydrogenation.

8. The method of preparing 3-DPA-lactone according to claim 1, wherein in step (d), the protecting group R for the hydroxyl group of the compound represented by formula (4) is eliminated by a reaction under a basic condition or acidic condition.

9. The method of preparing 3-DPA-lactone according to claim 1, wherein step (a) is performed in the presence of an organic solvent.

10. The method of preparing 3-DPA-lactone according to claim 1, wherein step (a) is carried out at a temperature of 0° to 40° C. for 10 to 120 minutes.

11. The method of preparing 3-DPA-lactone according to claim 1, wherein in step (a), the hydroxyl groups at the 2- and 5-positions of γ-ribonolactone are protected using 2 to 3 equivalents of a reagent having said protecting group R per one equivalent of γ-ribonolactone.

12. The method of preparing 3-DPA-lactone according to claim 3, wherein step (b) is carried out at a temperature of 0° to 40° C. for 0.5 to 20 hours.

13. The method of preparing 3-DPA-lactone according to claim 3, wherein step (b) is carried out at room temperature for 0.5 to 20 hours.

14. The method of preparing 3-DPA-lactone according to claim 3, wherein in step (b), the hydroxyl group at the 3-position of the compound represented by formula (2) is converted into a leaving group by using 1 to 10 equivalents of a compound having said leaving group per one equivalent of the compound represented by formula (2).

15. The method of preparing 3-DPA-lactone according to claim 3, wherein the d-eliminator reaction is carried out in the presence of a tertiary amine compound.

16. The method of preparing 3-DPA-lactone according to claim 15, wherein said tertiary amine compound is pyridine.

17. The method of preparing 3-DPA-lactone according to claim 7, wherein said catalytic hydrogenation is in the presence of a metal catalyst selected from the group consisting of platinum, palladium, rhodium, and ruthenium.

18. The method of preparing 3-DPA-lactone according to claim 17, wherein said catalytic hydrogenation is carried out in an organic solvent selected from the group consisting of ethyl acetate, ethanol, and methanol, under hydrogen atmosphere at room temperature.

19. The method of preparing 3-DPA-lactone according to claim 17, wherein said catalytic hydrogenation is carried out by using 0.01 to 1 equivalent of said metal catalyst per one equivalent of the compound represented by formula (3).

20. The method of preparing 3-DPA-lactone according to claim 1, wherein step (c) is carried out at a temperature of 10° to 40° C. for 0.5 to 15 hours.

* * * * *